(12) United States Patent
Rampalli et al.

(10) Patent No.: US 9,790,185 B2
(45) Date of Patent: Oct. 17, 2017

(54) PROCESS FOR THE PREPARATION OF REGORAFENIB AND ITS CRYSTALLINE FORMS

(71) Applicant: SHILPA MEDICARE LIMITED, Raichur,karnataka (IN)

(72) Inventors: Sriram Rampalli, Vizianagaram (IN); Lav Kumar Upalla, Vizianagaram (IN); Krishna Kumar Ramachandrula, Vizianagaram (IN); Prashant Purohit, Raichur (IN); Chaturvedi Akshay Kant, Raichur (IN)

(73) Assignee: SHILPA MEDICARE LIMITED, Karnataka ( * ) Notice: Subject to any disclaimer, the term of this patent is extended or adjusted under 35 U.S.C. 154(b) by 0 days.

(21) Appl. No.: 15/324,683

(22) PCT Filed: Jul. 6, 2015

(86) PCT No.: PCT/IB2015/055083
§ 371 (c)(1),
(2) Date: Jan. 7, 2017

(87) PCT Pub. No.: WO2016/005874
PCT Pub. Date: Jan. 14, 2016

(65) Prior Publication Data
US 2017/0204062 A1    Jul. 20, 2017

(30) Foreign Application Priority Data

Jul. 9, 2014  (IN) .......................... 3391/CHE/2014
Jul. 9, 2014  (IN) .......................... 3396/CHE/2014

(51) Int. Cl.
C07D 213/81    (2006.01)

(52) U.S. Cl.
CPC .................. *C07D 213/81* (2013.01)

(58) Field of Classification Search
None
See application file for complete search history.

(56) References Cited

U.S. PATENT DOCUMENTS

| | | |
|---|---|---|
| 7,351,834 B1 | 4/2008 | Riedl et al. |
| 8,637,553 B2 | 1/2014 | Boyer et al. |
| 2006/0058358 A1 | 3/2006 | Dumas et al. |
| 2010/0063112 A1 | 3/2010 | Grunenberg et al. |
| 2010/0113533 A1 | 5/2010 | Stiehl et al. |
| 2010/0173953 A1 | 7/2010 | Grunenberg et al. |
| 2013/0116442 A1 | 5/2013 | Stiehl et al. |

FOREIGN PATENT DOCUMENTS

WO    2005009961 A2    2/2005

*Primary Examiner* — Zinna Northington-Davis

(57) ABSTRACT

The present invention relates to a process for the preparation of 4-[4-({[4-chloro-3-(trifluoromethyl)phenyl]carbamoyl}amino)-3-fluorophenoxy]-N-methylpyridine-2-carboxamide or Regorafenib (I).

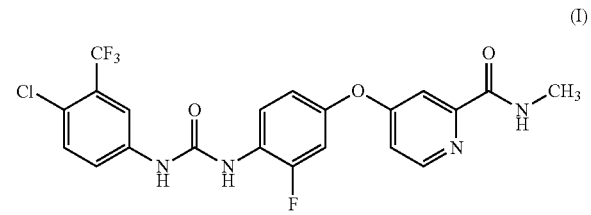

The present invention further relates to a process for the purification of 4-[4-({[4-chloro-3-(trifluoromethyl) phenyl]carbamoyl} amino)-3-fluorophenoxy]-N-methylpyridine-2-carboxamide or Regorafenib (I) to provide highly pure material.

The present invention further relates to a process for the preparation stable crystalline material of 4-[4-({[4-chloro-3-(trifluoromethyl)phenyl]carbamoyl}amino)-3-fluorophenoxy]-N-methyl pyridine-2-carboxamide or Regorafenib (I) useful in the preparation of pharmaceutical compositions for the treatment of cancer.

8 Claims, 2 Drawing Sheets

PROCESS FOR THE PREPARATION OF REGORAFENIB AND ITS CRYSTALLINE FORMS

The present invention relates to a process for the Regorafenib of Formula (I).

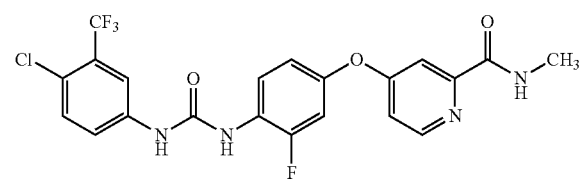

The present invention farther relates to a process for the purification of Regorafenib The present invention futher relates to a process for the preparation crystalline forms of Regorafenib of Formula (I).

BACKGROUND OF THE INVENTION

4-[4-({[4-chloro-3-(trifluoromethyl)phenyl]carbamoyl}amino)-3-fluorophenoxy]-N-methylpyridine-2-carboxamide or Regorafenib is low molecular weight, orally available, inhibitor of multiple protein kinases, including kinases involved in tumour angiogenesis (VEGFR1, -2, -3, TIE2), oncogenesis (KIT, RET, RAF-1, BRAF, BRAFV600E), and the tumour microenvironment (PDGFR, FGFR). In preclinical studies regorafenib has demonstrated antitumour activity in a broad spectrum of tumour models including colorectal tumour models which is mediated both by its antiangiogenic and antiproliferative effects. Major human metabolites (M-2 and M-5) exhibited similar efficacies compared to Regorafenib both in vitro and in vivo models.

Regorafenib was approved USFDA, in 2012 and is marketed under the brand name Stivarga®, is an important chemotherapeutic agent useful for the treatment of adult patients with metastatic colorectal cancer (CRC) who have been previously treated with, or are not considered candidates for, available therapies. These include fluoropyrimidine-based chemotherapy, an anti-VEGF therapy and an anti-EGFR therapy.

Regorafenib is chemically known as 4-[4-({[4-chloro-3-(trifluoromethyl) phenyl]carbamoyl} amino)-3-fluorophenoxy]-N-methylpyridine-2-carboxamide (I). Regorafenib is a white to slightly pink or slightly brownish solid substance with the empirical formula $C_{21}H_{15}ClF_4N_4O_3$ and a molecular weight of 482.82. Regorafenib is practically insoluable in water, dilute alkaline, solution, dilute acid solution n-heptane glycerine and toluene. It is slightly soluble in acetonitrile, dichloromethane, propylene glycol, methanol, 2-propanol, ethanol and ethyl acetate. It is sparingly soluble in acetone and soluble in PEG 400 (macrogol). Regorafenib is not hygroscopic.

Regorafenib is generically disclosed in U.S. Pat. No. 7,351,834, d specifically disclosed in U.S. Pat. No. 8,637,553. US '553 discloses process for the preparation of Regorafenib starting from 3-fluoro-4-nitrophenol. The process is as demonstrated below:

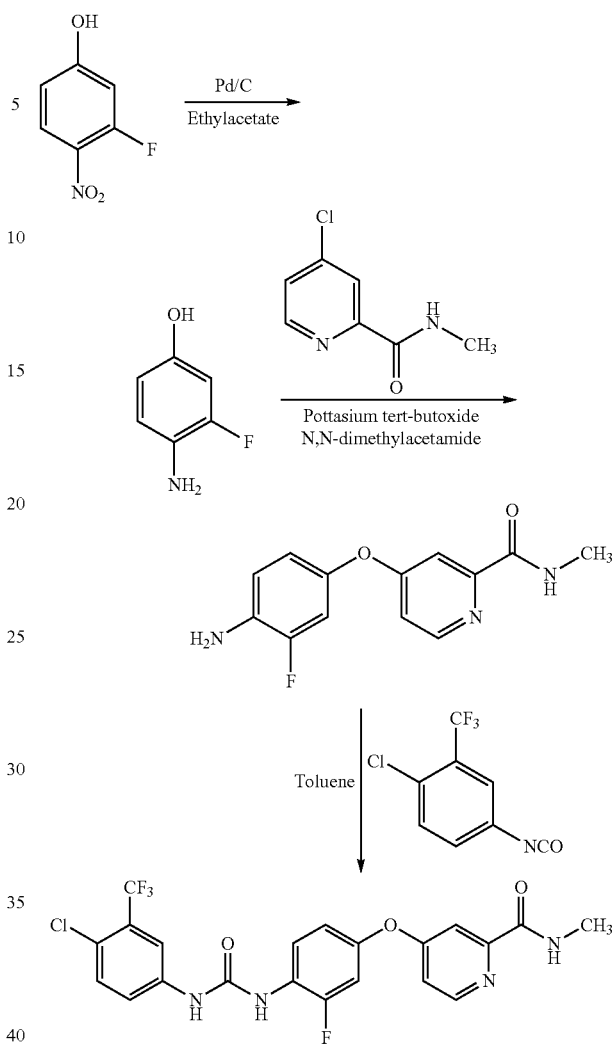

The present inventors has repeated the above process and found the following disadvantages:
  Unwanted reactions are observed during the formation of Regorafenib due to the time in process.
  Incomplete reactions were observed with excessive impurity formations due to incomplete conversion.
  Removal of impurities from final product US 2010173953 disclose Regorafenib monohydrate and crystalline Form I of Regorafenib. This patent application further discloses that crystalline Form I of Regorafenib stated in this application is obtained as per the process disclosed in WO 2005009961 A2 (Equivalent to US '553). The compound obtained was having a melting point of 186-206° C.

This patent publication discloses a process for the preparation of Regorafenib monohydrate comprises dissolving Regorafenib Form I obtained as per WO '961 in acetone and the solution is filtered, followed by addition of water until precipitation, which was filtered and dried at room temperature US 2010/0113533 discloses crystalline. Form II of Regorafenib, comprises dissolving Regorafenib Form I obtained as per WO '961 in ethyl acetate, the suspension was heated to 40-45° C., addition of isocyanate solution (isocyanate in ethyl acetate) and is cooled to room temperature to yield the crystals., which was filtered, washed with ethyl acetate and dried at room temperature.

US 2010/0063112 discloses Form III of Regorafenib, process comprises of heating Regorafenib monohydrate at 100° C. or 60 min, and further 15 min at 110° C., followed by cooling to room temperature.

As polymorphism has been given importance in the recent literatures owing to its relevance to the drugs having oral dosage forms due to its apparent relation to dose preparation/suitability in composition steps/bioavailability and other pharmaceutical profiles, stable polymorphic form of a drug has often remained the clear choice in compositions due to various reasons of handling, mixing and further processing including bioavailability and stability.

Exploring new process for these stable polymorphic forms which are amenable to scale up for pharmaceutically active/useful compounds such as 4-[4-({[4-chloro-3-(trifluoromethyl)phenyl]carbamoyl}amino)-3-fluorophenoxy]-N-methylpyridine-2-carboxamide or Regorafenib may thus provide an opportunity to improve the drug performance characteristics of such products.

Hence, inventors of the present application report a process for the preparation of a stable and usable form of 4-[4-({[4-chloro-3-(trifluoromethyl)phenyl]carbamoyl}amino)-3-fluorophenoxy]-N-methylpyridine-2-carboxamide Regorafenib, which may be industrially amenable and usable for preparing the corresponding pharmaceutical compositions. The present invention provides an improved process for the preparation of 4-[4-({[4-chloro-3-(trifluoromethyl)phenyl]carbamoyl}amino)-3-fluorophenoxy]-N-methylpyridine-2-carboxamide or Regorafenib crystalline forms specifically for crystalline polymorphic forms Form I and Form III. Crystalline polymorphic forms of 4-[4-({[4-chloro-3-(trifluoromethyl)phenyl]carbamoyl}amino)-3-fluorophenoxy]-N-methylpyridine-2-carboxamide or Regorafenib obtained by the process of the present invention is non-hygroscopic and chemically stable and has good dissolution properties.

In view of the above and to overcome the prior-art problems the present inventors had now developed an improved process for the preparation of Regorafenib, using industrially feasible and viable process, with the use of industrially friendly solvents, which does not include tedious work up and time lagging steps.

OBJECTIVE OF THE INVENTION

The main objective of the invention relates to aprocess for the preparation of 4-[4-({[4-chloro-3-(trifluoromethyl)phenyl]carbamoyl}amino)-3-fluorophenoxy]-N-methylpyridine-2-carboxamide or Regorafenib (I).

Yet another objective of the invention relates to a process for the purification of 4-[4-({[4-chloro-3-(trifluoromethyl)phenyl]carbamoyl}amino)-3-fluorophenoxy]-N-methylpyridine-2-carboxamide or Regorafenib (I)

Yet another objective of the invention relates to a process for the preparation of anhydrous Regorafenib crystalline Form-I from Regorafenib or Regorafenib hydrate or solvate.

Yet another objective of the invention relates to a process for the preparation of Regorafenib crystalline Form III from Regorafenib.

Yet another objective of the invention relates to a process for the preparation of anhydrous Regorafenib crystalline Form-I from Regorafenib form III.

SUMMARY OF THE INVENTION

The present invention relates to a process for the preparation of 4-[4-({[4-chloro-3-(trifluoromethyl)phenyl]carbamoyl}amino)-3-fluorophenoxy]-N-methylpyridine-2-carboxamide (I)

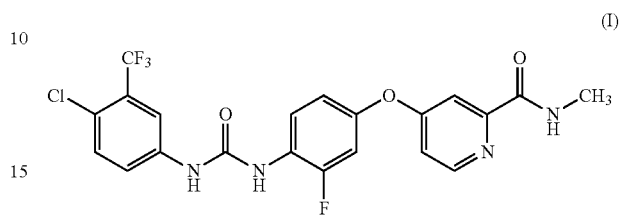

comprising the steps of:
a) adding 4-Chloro-N-methyl-2-pyridinecarboxamide of Formula II

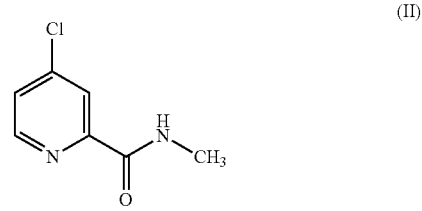

and 4-Amino-3-flurophenol of Formula III

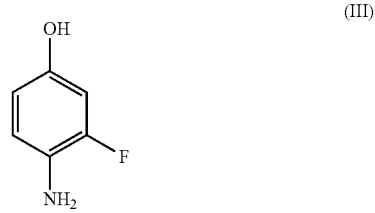

in an organic solvent in ratio between 3-8 v/w times with respect to compound of formula (II) at a temperature ranging between 20-35° C.;

b) reacting the mixture of step a) in presence of sodium/potassium tertiary butoxide in tetrahydrofuran to provide 4-(4-amino-3-fluorophenoxy) pyridine-2-carboxylic acid methyl amide (IV);

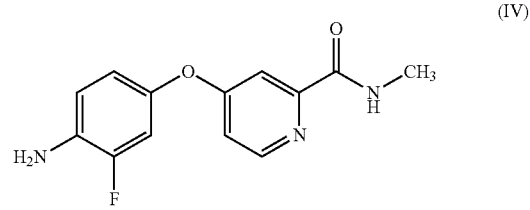 [SMILES: CNC(=O)c1cc(Oc2ccc(N)c(F)c2)ccn1]

c) reacting the compound of Formula IV with 4-chloro-3-trifluoromethylisocyanate of Formula V

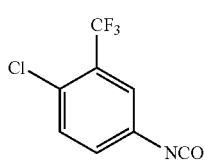

(V)

in presence of polar solvent in ratio between 3-8 v/w times with respect to compound of formula (IV) to provide 4-[4-({[4-chloro-3-(trifluoromethyl) phenyl] carbamoyl}amino)-3-fluorophenoxy]-N-methylpyridine-2-carboxamide(I); and d) optionally, purifying the 4-[4-({[4-chloro-3-(trifluoromethyl) phenyl]carbamoyl}amino)-3-fluorophenoxy]-N-methylpyridine-2-carboxamide using a polar solvent or a mixture of polar and hydrocarbon solvent.

In another aspect of the invention relates to 4-[4-({[4-chloro-3-(trifluoromethyl) phenyl]carbamoyl}amino)-3-fluorophenoxy]-N-methylpyridine-2- carboxamide having purity greater than 99.5% and substantially free from process related impurities:

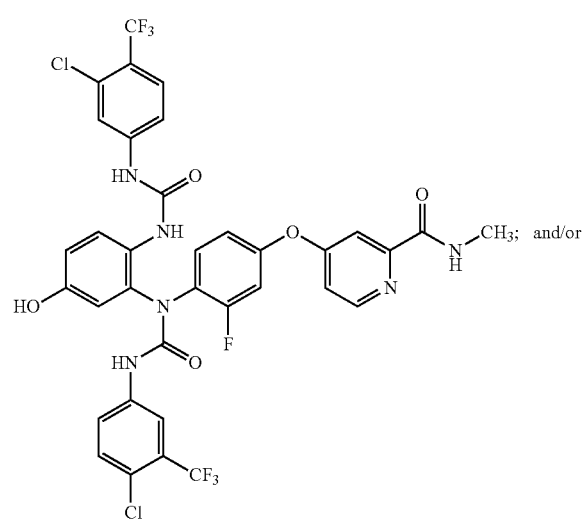

(A)

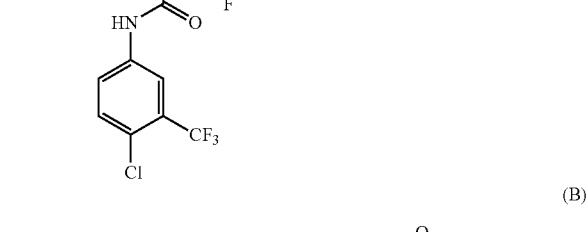

(B)

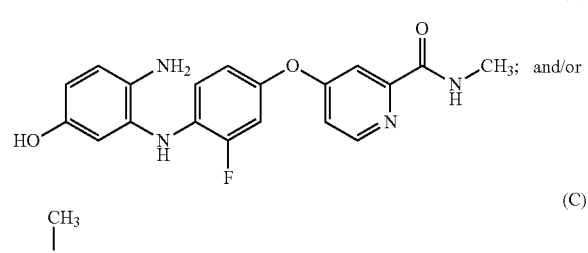

(C)

In yet another aspect of the invention relates to a process for the purification of 4-[4-({[4-chloro-3-(trifluoromethyl) phenyl]carbamoyl}amino)-3-fluorophenoxy]-N-methyl-pyridine-2-carboxamide (I) comprising the steps of a) stirring 4-[4-({[4-chloro-3-(trifluoromethyl) phenyl] carbamoyl}amino)-3-fluorophenoxy]-N-methylpyridine-2-carboxamide in a polar or mixture of polar and hydrocarbon solvent up to reflux temperature;

b) recovering pure 4-[4-({[4-chloro-3-(trifluoromethyl) phenyl]carbamoyl}amino)-3-fluorophenoxy]-N-methylpyridine-2-carboxamide (I) substantially free from process related impurities (A), (B) and (C); and/or c) optionally, repeating step a) & b) to get desired purity.

In yet another aspect of the invention relates to a process for the preparation of anhydrous Regorafenib crystalline Form-I comprising the steps of a) stirring Regorafenib or Regorafenib hydrate or solvate with a polar or mixture of polar and hydrocarbon solvent at reflux temperature;

b) cooled to 0-10° C.; and c) isolating crystalline Form I of Regorafenib

Another aspect of the invention related to a process for the preparation of Regorafenib crystalline Form III comprising the steps of— a) providing a solution of Regorafenib with an alcohol solvent;

b) stir the solution at temperature ranging between 50-90° C. for a time duration between 15-90 minutes;

c) cooled to mixture: between 0-10° C.; and d) isolating pure crystalline Form III Regorafenib Yet another aspect of the invention relates to a process for the preparation of anhydrous Regorafenib crystalline Form-I comprising the steps of— a) stirring Regorafenib crystalline Form III with a polar or mixture of polar and hydrocarbon solvent at 50-70° C.;

b) cooled to 0-10° C.; and c) isolating crystalline Form I of Regorafenib

DETAILED DESCRIPTION OF THE INVENTION

Figure 1:
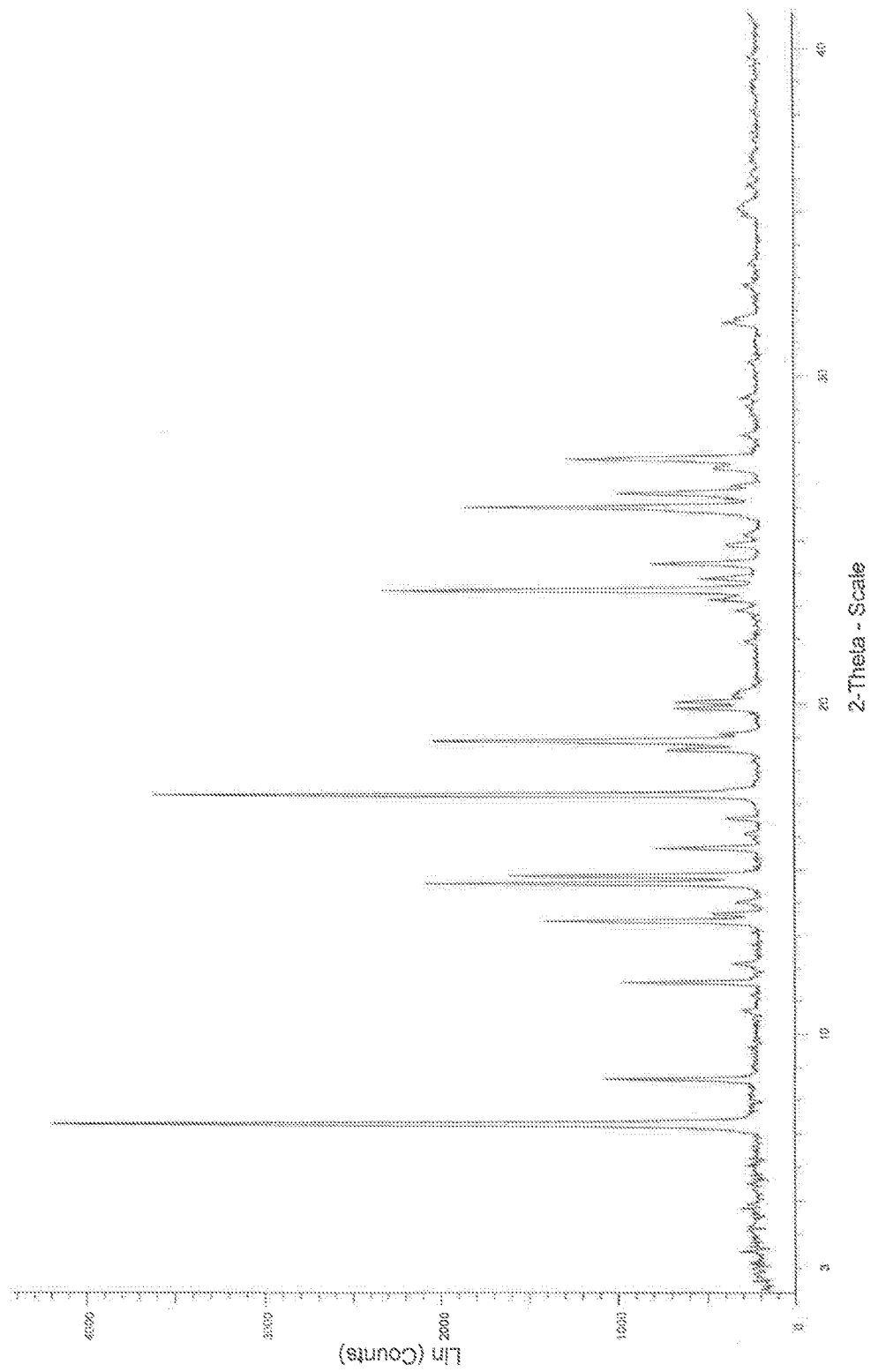
FIG. 1 is an example of X-ray powder diffraction XRP pattern of Regorafenib (I) obtained according to the process of the present invention.

The present invention relates to a process for the preparation of 4-[4-({[4-chloro-3-(trifluoromethyl)phenyl] carbamoyl}amino)-3-fluorophenoxy]-N-methylpyridine-2-carboxamide or Regorafenib (I) comprising adding 4-Chloro-N-methyl-2-pyridinecarboxamide (II) and 4-Amino-3-fluorophenol (III) in an organic solvent Selected from amide solvents such as formamide, dimethyl formamide, N-methyl-2-pyrrolidone N-methyl formamide, N-vinyl acetamide, N-vinyl pyrrolidone, 2-pyrrolidone; in the ratio between 3-8 v/w times with respect to compound of formula (II) at a temperature ranging between 20-35° C. The obtained reaction mixture was heated to 110-115° C. and then a solution of sodium/potassium tertiary butoxide in tetrahydrofuran was added slowly over a period of 3 to 4 hours. Distill off the solvent without vacuum, followed by pH adjustment with Hydrochloric acid to obtain crude 4-(4-amino-3-fluorophenoxy) pyridine-2-carboxylic acid methyl amide (IV). The obtained crude material finally recrystallized with ethyl acetate to provide 4-(4-amino-3-fluorophenoxy) pyridine-2-carboxylic acid methyl amide (IV).

In one embodiment, the present inventor's surprisingly found that use of an organic solvent in the ratio between 3-8 v/w times with respect to compound of formula (II) leads to provide 4-(4-amino-3-fluorophenoxy) pyridine-2-carboxylic acid methyl amide (IV) in higher yields compare to the prior-art process.

On the other hand, the prior art processes involves the use of excess solvent greater than 8 v/w times, which involves distillation of solvent at high temperature leads in the decomposition of product and lowering the quantity of yield. The present inventors also found that the use of excess solvent also leads in the conversion of reactant in the range of 70-75% only, which means that the reaction becomes incomplete.

The present inventors also found that the use of an organic solvent in the ratio between 3-8 v/w times with respect to compound of formula (II) is advantageous while removing the solvent after completion of the reaction, which is very easy and does not require any cumbersome workup.

In another embodiment, the present inventors surprisingly found that the use of sodium/potassium tertiary butoxide in tetrahydrofuran instead of anhydrous sodium/potassium tertiary butoxide is advantageous over prior art, as the reaction completes within hours and conversion is also greater than 95%. This is due to the decomposition activity of anhydrous sodium/potassium tertiary butoxide, which is overcome by using a solution of sodium/potassium tertiary butoxide completes the reaction within hours, which is industrially feasible and economical. Further, use of sodium/potassium tertiary butoxide solution completes the reaction within hours also helps in avoiding the unwanted reactions and minimizes the formation of impurity in the formation 4-(4-amino-3-fluorophenoxy) pyridine-2-carboxylic acid methyl amide (IV).

4-chloro-3-trifluoromethylisocyanate was added slowly over a period of 5 to 10 minutes to the solution of 4-(4-amino-3-fluorophenoxy) pyridine-2-carboxylic acid methyl amide (IV), wherein the solution was obtained by dissolving 4-(4-amino-3-fluorophenoxy) pyridine-2-carboxylic acid methyl amide (IV) in a polar sorest selected from ketone solvents such as acetone, methyl ethyl ketone, methyl isopropyl ketone, methyl isobutyl ketone (MIBK); amide solvents such as formamide, dimethyl formamide, N-methyl-2-pyrrolidone, N-methyl formamide, N-vinylacetamide, N-vinyl pyrrolidone, 2-pyrrolidone; alcohols, such as methanol, ethanol, isopropanol; ethers such as tetrahydrofuran, dioxane; water or mixtures thereof in ratio between 3-8 v/w times with respect to compound of formula (IV) at a temperature ranging from 25-30° C.; by continuous stirring for 3 to 4 hours; followed by washing with tolueneto provide, 4-[4-({[4-chloro-3-(trifluoromethyl) phenyl]carbamoyl}amino)-3-fluorophonoxy]-N-methylpyridine-2-carboxamide(I);

In an another embodiment, the present inventors surprisingly found that the use of polar solvent in the condensation of 4-chloro-3-trifluoromethylisocyanate (V) with 4-(4-amino-3-fluorophenoxy) pyridine-2-carboxylic acid methyl amide (IV) completes the reactions within 3 to 5 hours, which is industrially feasible and economical.

The present inventors also found that the use of polar solvent in the condensation of 4-chloro-3-trifluoromethylisocyanate (V) with 4-(4-amino-3-fluorophenoxy) pyridine-2-carboxylic acid methyl amide (IV) leads to provide higher yields, compare to the prior processes known in the art, which is more advantageous in industrial scale.

The present inventors also found that the use of polar solvent in the condensation of 4-chloro-3-trifluoromethylisocyanate (V) with 4-(4-amino-3-fluorophenoxy) pyridine-2-carboxylic acid methyl amide (IV) leads to formation of 4-[4-({[4-chloro-3-(trifluoromethyl) phenyl] carbamoyl}amino)-3-fluorophenoxy]-N-methylpyridine-2-carboxamide (I), immediately after completion of the reaction and does not require cumbersome workup.

4-[4-({[4-chloro-3-(trifluoromethyl) phenyl]carbamoyl} amino)-3-fluorophenoxy]-N-methylpyridine-2-carboxamide (I) obtained above is purified using a polar solvent selected from selected from ketone solvents such as acetone, methyl ethyl ketone, methyl isopropyl ketone, methyl isobutyl ketone (MIBK); amide solvents such as formamide, dimethyl formamide, N-methyl-2-pyrrolidone, N-methyl formamide, N-vinylacetamide, N-vinyl pyrrolidone, 2-pyrrolidone; alcohols, such as methanol, ethanol, isopropanol; ethers such as tetrahydrofuran, dioxane; water or mixtures thereof or a mixture of polar and hydrocarbon solvent selected from selected from toluene, xylene, cyclohexane, hexane; halogenated hydrocarbons such as methylene dichloride, ethylene chloride, chloroform; or mixtures thereof; at a temperature ranging from 60-110° C., by stirring the reaction mixture for 15 to 45 minutes, cooling to room temperature and continued stirring for 30 minutes to 2 hours; the obtained reaction mixture was filtered and washed with toluene to yield pure 4-[4-({[4-chloro-3-(trifluoromethyl) phenyl]carbamoyl}amino)-3-fluorophenoxy]-N-methylpyridine-2-carboxamide (I) or Regorafenib.

Drying may be also be performed by any conventional process not limited to spray drying or distillation to remove the solvent. Drying may be performed under reduced pressure conditions also. Reduced pressure conditions may be suitably utilized by person skilled in the art in order to obtain the dried material. The drying may be performed at a temperature ranging from 50-65° C. for a time ranging from 12 to 16 hours depending upon the physical attributes of the end product obtained i.e. Pure Regorafenib. 4-[4-({[4-chloro-3-(trifluoromethyl)phenyl]carbamoyl}amino)-3-fluorophenoxy]-N-methylpyridine-2-carboxamide(I) or Regorafenib obtained according to the present invention is having purity greater than 99.5%.

The obtained pure 4-[4-({[4-chloro-3-(trifluoromethyl) phenyl]carbamoyl}amino)-3-fluorophenoxy]-N-methyl-pyridine-2-carboxamide (I) or Regorafenib having purity greater than 99.5% and substantially free from process related impurities:

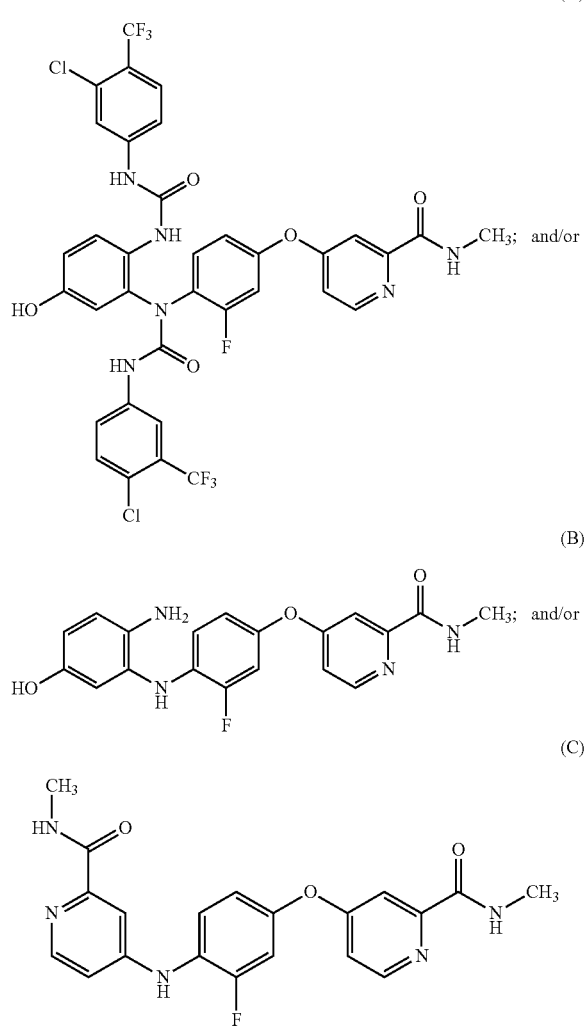

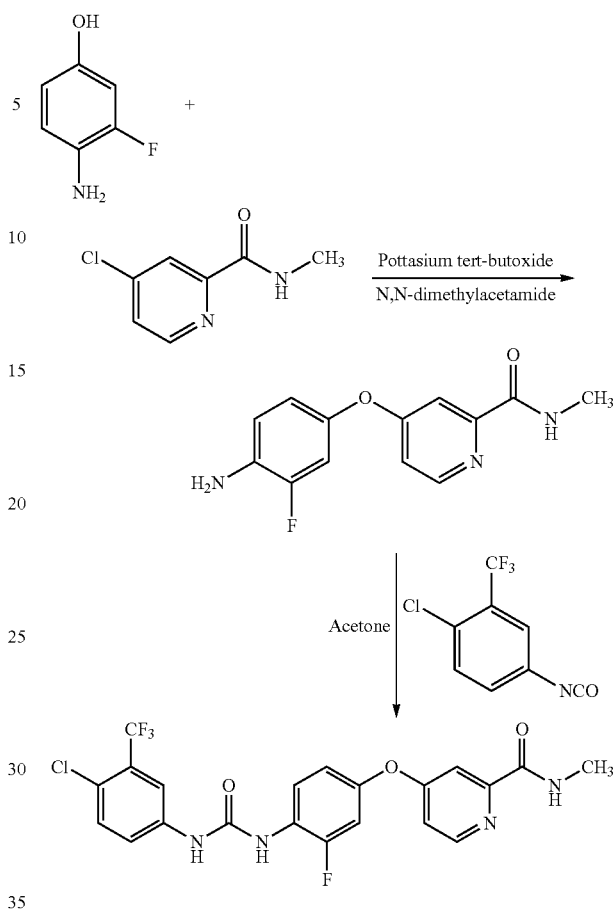

Regorafenib obtained according to the present invention is analyzed by PXRD and obtained PXRD pattern having diffraction angle values at 7.2, 8.6, 11.5, 12.0, 13.4, 14.5, 14.8, 15.6, 16.5, 17.2, 17.4, 18.6, 18.8, 19.0, 19.8, 20.0, 20.2, 23.4, 23.8, 24.2, 24.8, 25.8, 25.9, 26.3, 26.4, 26.6, 27.2, 27.4 and 31.6±0.2°2θ

The crystalline Form I of Regorafenib produced by following the process described in the present invention was further analyzed by powder X-ray diffraction, which is similar to the XRPD pattern characterized similar to as shown in FIG. 1

Any Regorafenib (I) i.e. its crystalline form or hydrate or solvate or any of its less stable form or impure form obtained from any source or by any of the processes known in the prior art may be utilized as a starting material and result directly in the crystalline Form I of Regorafenib (I) of the present invention, by using the process mentioned in this application.

The process related impurities that appear in the impurity profile of the Regorafenib may be substantially removed by the process of the present invention resulting in the formation of highly pure material. The process of the present invention is as summarized below:

The process related impurities that appear in the impurity profile of the Regorafenib (I) may be substantially removed by the process of the present invention resulting in the formation of crystalline Form I of Regorafenib (I) of high purity.

The merit of the process according to the present invention resides in that product isolated after drying is directly obtained as crystalline Form I of Regorafenib (I). Said material is found devoid of any other crystal lattice and is adequately stable to handle and store for longer time (at least up to more than 6 months) without any significant or measurable change in its morphology and physicochemical characteristics. Crystalline Form I of Regorafenib (I) obtained according to the process of the present invention results in the final API purity by of more than 99.5% w/w, and found to be anhydrous with moisture content of not more than 0.5%.

In another embodiment the present invention relates process for the preparation of Regorafenib crystalline Form III comprising, providing a solution of Regorafenib with an alcohol solvent selected from isopropanol, n-butanol, isobutanol or isoamyl alcohol or mixtures thereof; stir the solution at temperature ranging between 50-90° C. for a time duration between 15 to 90 minutes; cooled the reaction mixture to room temperature and stirred for 20 hours; further cooled the reaction mixture between 0-10° C. and stirred for 2 to 3 hours; filtered the material and washed with the corresponding alcohol and water mixture to isolate pure crystalline Form III of Regorafenib.

Figure 2:
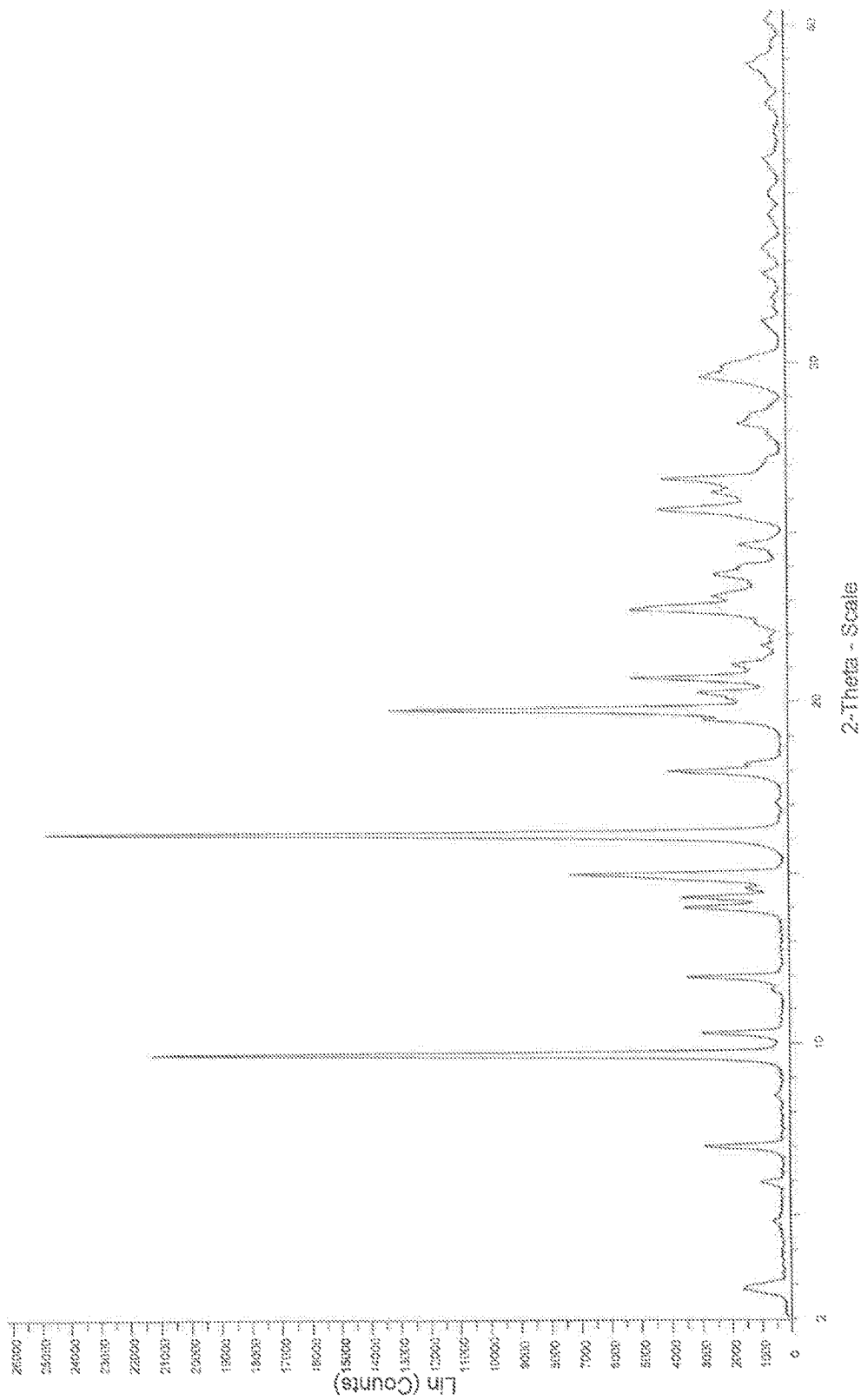
FIG. 2 is an example of X-ray powder diffraction ("XRPD") pattern of crystalline Form III of Regorafenib (I) obtained according the present

The crystalline Form III of Regorafenib produced by following the process described in the present invention was further analyzed by powder X-ray diffraction, which is similar to the XRPD pattern characterized similar to as shown in FIG. 2.

Any Regorafenib (I) i.e. its crystalline form or hydrate or solvate or any of its less stable form or impure form obtained from any source or by any of the processes known in the prior art may be utilized as a starting material and result directly in the crystalline Form III of Regorafenib (I) of the present invention, by using the process mentioned in this application.

The process related impurities that appear in the impurity profile of the Regorafenib (I) may be substantially removed by the process of the present invention resulting in the formation of crystalline Form III of Regorafenib (I) of high purity.

The merit of the process according to the present invention resides in that product isolated after drying is directly obtained as crystalline Form III of Regorafenib (I). Said material is found devoid of any other crystal lattice and is adequately stable to handle and store for longer time (at least up to more than 6 months) without any significant or measurable change in its morphology and physicochemical characteristics. Crystalline Form III of Regorafenib (I) obtained according to the process of the present invention results in the final API purity by HPLC of more than 99.5% w/w, and found to be anhydrous with moisture content of not more than 0.5%.

In yet another embodiment the present invention relates to a process for the preparation of anhydrous Regorafenib crystalline Form-I comprising, stirring Regorafenib crystalline Form III with a polar solvent selected from ketone solvents such as acetone, methyl ethyl ketone, methyl isopropyl ketone, methyl isobutyl ketone (MIBK); amide solvents such as formamide, dimethyl formamide, N-methyl-2-pyrrolidone, N-methyl formamide, N-vinylacetamide, N-vinyl pyrrolidone, 2-pyrrolidone, N,N-dimethylacetamide; alcohols, such as methanol, ethanol, isopropanol; ethers such as tetrahydrofuran, dioxane; water or mixtures thereof; or mixture of polar and hydrocarbon solvent selected from toluene, xylene, cyclohexane, hexane; halogenated hydrocarbons such as methylene dichloride, ethylene chloride, chloroform; or mixtures thereof; at a temperature ranging front 50-70° C; Distill off solvent still 3-4 volumes of solvent remains in the flask; the obtained reaction mass was cooled to 0-10° C. and stirred for 15 to 90 minutes. The obtained reaction mass was filtered and washed with acetone to obtain pure Regorafenib crystalline Form-I.

The crystalline Form I of Regorafenib produced by following the process described in the present invention was further analyzed by powder X-ray diffraction, which is similar to the XRPD pattern characterized similar to as shown in FIG. 1.

In yet another embodiment the present invention relates to a process for the preparation of anhydrous Regorafenib crystalline Form-I comprising, stirring Regorafenib crystalline Form III with a acetone at a temperature ranging from 50-70° C.; Distill off acetone still 3-4 volumes of solvent remains in the flask; the obtained reaction mass was cooled to 0-10° C. and stirred for 15 to 90 minutes. The obtained reaction mass was filtered and washed with acetone to obtain pure Regorafenib crystalline Form-I.

The crystalline Form I of Regorafenib produced by following the process described in the present invention was further analyzed by powder X-ray diffraction, which is similar to the XRPD pattern characterized similar to as shown in FIG. 1.

In another embodiment, the Regorafenib obtained by the processes of the present application may be formulated as solid compositions for oral administration in the form of capsules, tablets, pills, powders or granules. In these compositions, the active product is mixed with one or more pharmaceutically acceptable excipients. The drug substance can be formulated as liquid compositions for oral administration including solutions, suspensions, syrups, elixirs and emulsions, containing solvents or vehicles such as water, sorbitol, glycerine, propylene glycol or liquid paraffin.

The compositions for parenteral administration can be suspensions, emulsions or aqueous or non-aqueous sterile solutions. As a solvent or vehicle, propylene glycol, polyethylene glycol, vegetable oils, especially olive oil, and injectable organic esters, e.g. ethyl oleate, may be employed. These compositions can contain adjuvants, especially wetting, emulsifying and dispersing agents. The sterilization may be carried out in several ways, e.g. using a bacteriological filter, by incorporating sterilizing agents in the composition, by irradiation or by heating. They may be prepared in the form of sterile compositions, which can be dissolved at the time of use in sterile water or any other sterile injectable medium.

Pharmaceutically acceptable excipients used in the compositions comprising Regorafenib obtained as per the present application process—include, but are but not limited to diluents such as starch, pregelatinized starch, lactose, powdered cellulose, microcrystalline cellulose, dicalcium phosphate, tricakium phosphate, mannitol, sorbitol, sugar and the like; binders such as acacia, guar gum, tragacanth, gelatin, pre-gelatinized starch and the like; disintegrants such as starch, sodium starch glycolate, pregelatinized starch, Croscarmellose sodium, colloidal silicon dioxide and the like; lubricants such as stearic acid, magnesium stearate, zinc stearate and the like; glidants such as colloidal silicon dioxide and the like; solubility or wetting enhancers such as anionic or cationic or neutral surfactants, waxes and the like. Other pharmaceutically acceptable excipients that are of use include but not limited to film formers, plasticizers, colorants, flavoring agents, sweeteners, viscosity enhancers, preservatives, antioxidants and the like.

Pharmaceutically acceptable excipients used in the compositions derived from Regorafenib of the present application may also comprise to include the pharmaceutically acceptable carrier used for the preparation of solid dispersion, wherever utilized in the desired dosage form preparation.

The following examples illustrate the nature of the invention and are provided for illustrative purposes only and should not be construed to limit the scope of the invention.

EXAMPLES

Example 1

Preparation of 4-(4-amino-3-fluorophenoxy) pyridine-2-carboxylic acid methyl amide 4-Amino-3-fluorophenol (11 g, 00.8 moles) and of 4-Chloro-N-methyl-2-pyridinecarboxamide (8.85 g, 0.05 moles) was added to a reaction flask containing N,N-dimethylacetamide (55 ml) at 25-30° C. and stirred for 15 minutes. The reaction mixture was heated to 110-115° C. and then potassium tert-butoxide in tetrahydrofuran (60 ml, 0.06 moles) was added slowly over a period of 3 to 4 hours. Distill off solvent at same temperature, cooled the reaction mass to 25-30° C. and water (110 ml) was added slowly over a period of 15 min. and cooled the reaction mass to 0-5° C. Adjust the pH of the reaction mass in between 7 and 7.5 by using 10% aqueous hydrochloric acid (~7 ml). Stir the reaction mass for 30 min at the same temperature. Filter the product, washed with water (22 mL) and Dried at 50-55° C. for 12 hrs. The obtained crude material was added to the flask containing Ethyl acetate (55 mL). The reaction mass was heated to reflux to get a clear solution and stirred for 15 min at reflux. Cooled to 0-5° C., stir for 2 hrs at the same temperature. Filter the product, washed with Toluene (9 mL) and dried at 50-55° C. for 3-5 hrs.

Above recrystallized material was added to the reaction flask containing methylene dichloride (270 mL) at 25-30° C. and stirred for 10-15 min. Activated carbon (1 g) and silica gel (4.4 g) was added to the reaction mass and stir for 1 h at the same temperature. Filter the reaction mass through hyflow bed and wash with methylene dichloride (18 mL). Distill off solvent ~1-2 volumes of methylene dichloride remains in the flask and then cooled to 25-30° C. Toluene (20 mL) was added and stirred for 30 min at the same temperature. Filtered the product, washed with Toluene (9 mL) and dried at 50-55° C. for 12 h.

Yield: 9 gm
Chromatographic Purity (By HPLC): 98%

Example 2

Preparation of Regorafenib 4-(4-amino-3-fluorophenoxy) pyridine-2-carboxylic acid methyl amide (4 g, 0.01 moles) was added in to a reaction flask containing acetone (20 ml) at 25-30° C. and stirred for 15 minutes. 4-chloro-3-trifluoromethylisocyanate (6.1 g, 0.02 moles) was added slowly over a period of 5 to 10 minutes and stirred the reaction mixture 3 to 4 hours. Toluene (20 mL) was added to the reaction mass and stirred for 30 min at 25-30° C. The obtained reaction mass was filtered and washed with toluene (8 mL). Dried the material still constant weight appears to yield title product a crystalline material:

Yield: 5.5 gm
Chromatographic Purity (By HPLC): 97%

Example 3

Purification of Regorafenib using Acetone and Toluene Mixture

4-[4-({[4-chloro-3-(trifluoromethyl)phenyl]carbamoyl}amino)-3-fluorophenoxy]-N-methylpyridine-2-carboxamide (I) or Regorafenib (1 g) was added slowly in to the reaction flask containing acetone (2 mL) and toluene (3 mL) at 25-30° C. and stirred for 15 minutes. The reaction mixture was heated to 50-55° C. and stirred the reaction Mixture for 30 minutes. Cooled the reaction mass to 25-30° C. and stirred for 1 hour. Filter the material, washed with toluene (2 mL) and suck dried for 15 min, followed by drying at 50-55° C. for 10-12 h to yield Pure 4-[4-({[4-chloro-3-(trifluoromethyl)phenyl]carbamoyl}amino)-3-fluorophenoxy]-N-methylpyridine-2-carboxamide (1) or Regorafenib.

Yield: 0.88 gm
Chromatographic Purity (By HPLC): 99.3%

Example 4

Purification of Regorafenib using Acetone

4-[4-({[4-chloro-3-(trifluoromethyl) phenyl]carbamoyl}amino)-3-fluorophenoxy]-N-methylpyridine-2-carboxamide (I) or Regorafenib (1 g) was added slowly in to the reaction flask containing acetone (5 mL) at 25-30° C. and stirred for 15 minutes. The reaction mixture was heated to 50-55° C. and stirred the reaction mixture for 30 minutes. Cooled the reaction mass to 0-5° C. and stirred for 1 hour. Filter the material, washed with acetone (1 mL) and suck dried for 15 min. The obtained wet cake was added in to the reaction flask containing acetone (5 mL) at 25-30° C. and stirred for 15 minutes. The reaction mixture was heated to 50-55° C. and stirred the reaction mixture for 30 minutes. Cooled the reaction mass to 0-5° C. and stirred for 1 hour. Filter the material, washed with acetone (1 mL) and dried at 60-65° C. or 12 h to yield Pure 4-[4-({[4-chloro-3-(trifluoromethyl)phenyl]carbamoyl}amino)-3-fluorophenoxy]-N-methylpyridine-2-carboxamide (I) or Regorafenib.

Yield: 0.7 gm
Chromatographic Purity (By HPLC): 99:77%

Example 5

Double—Purification of Regorafenib using Acetone and Toluene Mixture

4-[4-({[4-chloro-3-(trifluoromethyl) phenyl]carbamoyl}amino)-3-fluorophenoxy]-N-methylpyridine-2-carboxamide (I) or Regorafenib (1 g) was added slowly in to the reaction flask containing acetone (2 mL) and toluene (3 mL) at 25-30° C. and stirred for 15 minutes. The reaction mixture was heated to 50-55° C. and stirred the reaction mixture for 30 minutes. Cooled the reaction mass to 25-30° C. and stirred fort hour. Filter the material, washed with toluene (2 mL) and suck dried for 15 min. The obtained wet cake was added in to the reaction flask containing acetone (2 mL) and toluene (3 mixture at 25-30° C. and stirred for 15 minutes. The reaction mixture was heated to 50-55° C. and stirred the reaction mixture for 30 minutes. Cooled the reaction mass to 25-30° C. and stirred for 1 hour. Filter the material, washed with toluene (2 mL) and dry at 60-65° C. for 12 h.

Yield: 0.80 gm
Chromatographic Purity (By HPLC): 99.79%
Moisture content: 0.09%
Impurity-A: 0.03%
Impurity-B: Not detected
Impurity-C: 0.02%

Example 6

Preparation of Regorafenib Form I 4-(4-amino-3-fluorophenoxy) pyridine-2-carboxylic acid methyl amide (1.3 g, 0.004 moles) was added in to a reaction flask containing acetone (13 mL) at 25-30° C. and stirred for 15 minutes. 4-chloro-3-trifluoromethylisocyanate (6.6 g, 0.006 moles) was added slowly over a period of 15 to 20 minutes and stirred the reaction mixture 3 to 4 hours. The obtained reaction mass was filtered and washed with acetone. Dried the material still constant weight appears to yield title product a crystalline material.

Yield: 1.9 g
Chromatographic Purity (By HPLC): 98.4%
XRPD was found to resemble similar to FIG. 1.

Example 7

Preparation of Regorafenib Form I 4-(4-amino-3-fluorophenoxy) pyridine-2-carboxylic acid methyl amide (4 g, 0.01 moles) was added in to a reaction flask containing acetone (20 ml) at 25-30° C. and stirred for 15 minutes. 4-chloro-3-trifluoromethylisocyanate (6.1 g, 0.02 moles) was added slowly over a period of 5 to 10 minutes and stirred the reaction mixture 3 to 4 hours. Toluene (20 mL) was added to the reaction mass and stirred for 30 min at 25-30° C. The obtained reaction mass was filtered and washed with toluene (8 mL). Dried the material still constant weight appears to yield title product a crystalline material.

Yield: 5.5 g XRPD FIG. 1
Chromatographic Purity (By HPLC): ~99.5%

Example 8

Preparation of Regorafenib Form III

Regorafenib prepared as per reference example-2 (5 g, 0.01 moles) was charged in to a reaction flask containing Isoamylalcohol (140 mL) and water (35 mL) at 25-30° C. and sorted for 15 minutes. The obtained reaction mixture was heated to 80-85° C. and stirred the reaction mixture for 30 min. The obtained reaction mass was cooled to 25-30° C. and stirred for 20 hours. Cooled to 0-5° C. and stirred for 2h. The obtained reaction mass was filtered and washed with Isoamylalcohol and water mixture and dried still constant weigh appears to obtain the title product.

Yield: 4.5 g;
Chromatographic. Purity (By HPLC): 99.70%
XRPD was found to resemble similar to FIG. 2.
Moisture content: 0.23%

Example 9

Preparation of Regorafenib Form I from Regorafenib Form III

Regorafenib Form-III prepared as per reference example-4 (1 g, 0.02 moles) was charged in to a reaction flask containing acetone (25 ml) at 25-30° C. and stirred for 15 minutes. The obtained reaction mixture was heated to 50-55° C. and stirred the reaction mixture for 15 min. Distill off the solvent till 3-4 volumes of acetone remains in the flask. The obtained reaction mass was cooled to 0-5° C. and stirred for 30 min. The obtained reaction mass was filtered and washed with acetone and dried still constant weigh appears to obtain the title product.

Yield: 0.85 g
Chromatographic Purity (By HPLC): 99.73%
XRPD was found to resemble similar to FIG. 1.

The invention claimed is:
1. A process for the preparation of Regorafenib (I)

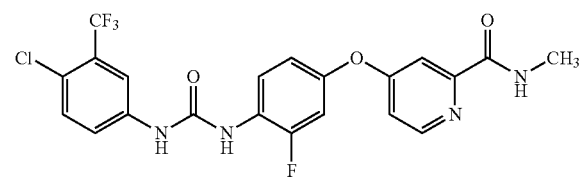

(I)

comprising the steps of:
a) adding 4-Chloro-N-methyl-2-pyridinecarboxamide of Formula II

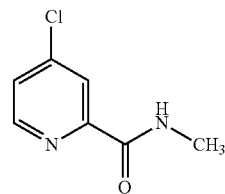

(II)

and 4-Amino-3-fluorophenol of Formula III

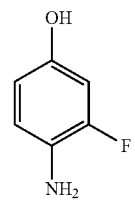

(III)

in an organic solvent in ratio between 3-8 v/w times with respect to compound of formula (II) at a temperature ranging between 20-35° C;
b) reacting the mixture of step a) in presence of sodium/potassium tertiary butoxide in tetrahydrofuran to provide 4-(4-amino-3-fluorophenoxy) pyridine-2-carboxylic acid methyl amide (IV);

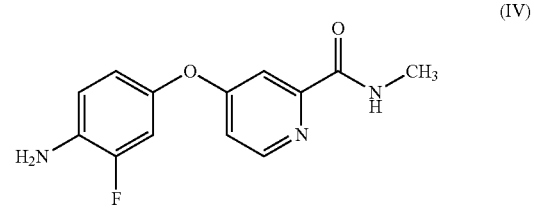 [SMILES: CNC(=O)c1cc(Oc2ccc(N)c(F)c2)ccn1]

(IV)

c) reacting the compound of Formula IV with 4-chloro-3-trifluoromethylisocyanate of Formula V

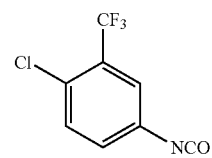

(V)

in presence of polar solvent in ratio between 3-8 v/w times with respect to compound of formula (IV) to provide Regorafenib (I); and
d) optionally, purifying the Regorafenib using a polar solvent or a mixture of polar and hydrocarbon solvent, wherein the degree of purity is 99.5%.

2. A process for the preparation of Regorafenib according to claim 1, wherein organic solvent used in step a) is selected from amide solvents formamide, dimethyl formamide, N-methyl-2-pyrrolidone, N-methyl formamide, N-vinylacetamide, N-vinyl pyrrolidone, 2-pyrrolidone, dimethyl acetamide.

3. A process for the preparation of Regorafenib according to claim 1, wherein polar solvent in step c) and d) are selected from ketone solvents acetone, methyl ethyl ketone, methyl isopropyl ketone, methyl isobutyl ketone (MIBK); amide solvents formamide, dimethyl formamide, N-methyl-2-pyrrolidone, N-methyl formamide, N-vinylacetamide, N-vinyl pyrrolidone, 2-pyrrolidone, dimethyl acetamide; alcohols, methanol, ethanol, isopropanol; ethers tetrahydrofuran, dioxane; water or mixtures thereof.

4. A process for the preparation of Regorafenib according to claim 1, wherein hydrocarbon solvent used in step d) is selected from toluene, xylene, cyclohexane, hexane; halogenated hydrocarbons methylene dichloride, ethylene chloride, chloroform; or mixtures thereof.

5. A process for the preparation of Regorafenib according to claim 1, wherein the product obtained is having PXRD pattern having diffraction angle values at 7.2, 8.6, 11.5, 12.0, 13.4, 14.5, 14.8, 15.6, 16.5, 17.2, 17.4, 18.6, 18.8, 19.0, 19.8, 20.0, 20.2, 23.4, 23.8, 24.2, 24.8, 25.8, 25.9, 26.3, 26.4, 26.6, 27.2, 27.4 and 31.6±0.2°2θ.

6. Regorafenib having purity greater than 99.5% and substantially free from process related impurities:

(A)

(B)

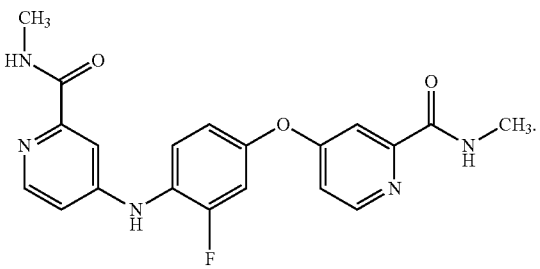

(C)

7. A process for the purification of Regorafenib (I)somprising the steps of a) stirring 4-[4-({[4-chloro-3-(trifluoromethyl)phenyl]carbamoyl}amino)-3-fluoro phenoxy]-N-methylpyridine-2-carboxamide in a polar or mixture of polar and hydrocarbon solvent up to reflux temperature;

b) recovering pure 4-[4-({[4-chloro-3-(trifluoromethyl)phenyl]carbamoyl}amino)-3-fluoro phenoxy]-N-methylpyridine-2-carboxamide (I) substantially free from process related impurities (A), (B) and (C); and/or c) optionally, repeating step a) & b) to get the desired purity of 99.5%.

8. A process for the preparation of Regorafenib according to claim 7, wherein polar solvent in step a) are selected from ketone solvents acetone, methyl ethyl ketone, methyl isopropyl ketone, methyl isobutyl ketone (MIBK); amide solvents formamide, dimethyl formamide, N-methyl-2-pyrrolidone, N-methyl formamide, N-vinylacetamide, N-vinyl pyrrolidone, 2-pyrrolidone, dimethyl acetamide; alcohols, methanol, ethanol, isopropanol; ethers tetrahydrofuran, dioxane; water or mixtures thereof; wherein hydrocarbon solvent used in step a) is selected from toluene, xylene, cyclohexane, hexane; halogenated hydrocarbons methylene dichloride, ethylene chloride, chloroform; or mixtures thereof.

* * * * *